(12) United States Patent
Kon et al.

(10) Patent No.: US 11,344,276 B2
(45) Date of Patent: *May 31, 2022

(54) CALIBRATION METHOD OF X-RAY MEASURING DEVICE

(71) Applicant: MITUTOYO CORPORATION, Kanagawa (JP)

(72) Inventors: Masato Kon, Kanagawa (JP); Hiromu Maie, Kanagawa (JP); Seiji Sasaki, Kanagawa (JP); Jyota Miyakura, Kanagawa (JP)

(73) Assignee: MITUTOYO CORPORATION, Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/015,618

(22) Filed: Sep. 9, 2020

(65) Prior Publication Data

US 2021/0068777 A1 Mar. 11, 2021

(30) Foreign Application Priority Data

Sep. 10, 2019 (JP) .............................. JP2019-164919

(51) Int. Cl.
*A61B 6/00* (2006.01)
*A61B 6/03* (2006.01)
*A61B 6/04* (2006.01)

(52) U.S. Cl.
CPC .............. *A61B 6/582* (2013.01); *A61B 6/032* (2013.01); *A61B 6/0407* (2013.01)

(58) Field of Classification Search
CPC ......... A61B 6/582; A61B 6/583; A61B 6/584; A61B 6/032; A61B 6/0407; G01N 2223/3306; G01N 2223/303; G01N 23/04; G01N 23/046; G01B 15/04; G01B 21/045

See application file for complete search history.

(56) References Cited

U.S. PATENT DOCUMENTS

2017/0020481 A1* 1/2017 Hawker ................ A61B 6/584
2021/0072022 A1* 3/2021 Kon ..................... G01B 15/045

FOREIGN PATENT DOCUMENTS

JP          2000-298105        10/2000

* cited by examiner

*Primary Examiner* — Courtney D Thomas
(74) *Attorney, Agent, or Firm* — Greenblum & Bernstein, P.L.C.

(57) ABSTRACT

A calibration method of an X-ray measuring device includes: mounting a calibration tool 102 on a rotating table 120; a moving position acquisition step of parallelly moving a position of an j-th sphere 106 with respect to a position of a first sphere 106, irradiating the calibration tool 102 with an X-ray 118, and acquiring, form an output of an X-ray image detector 124, a moving position Mj where the magnitude of a differential position Erjofa centroid position ImDisjh_Sphr_j of a projected image of the j(2£j£N)-th sphere 106 with respect to a centroid position ImDis1_Sphr_1 of a projected image of the first sphere 106 becomes equal to or less than a specified value Vx; a relative position calculation step of performing the moving position acquisition step on the remaining spheres; a feature position calculation step; a transformation matrix calculation step; a rotation detection step; a position calculation step; and a center position calculation step.

12 Claims, 5 Drawing Sheets

CALIBRATION METHOD OF X-RAY MEASURING DEVICE

CROSS-REFERENCE TO RELATED APPLICATION

The disclosure of Japanese Patent Application No. 2019-164919 filed on Sep. 10, 2019 including specifications, drawings and claims is incorporated herein by reference in its entirety.

TECHNICAL FIELD

The present invention relates to calibration methods of an X-ray measuring device, and particularly relates to a calibration method of an X-ray measuring device, the method allowing calculation of, for example, a rotation center position of a rotating table on which an object to be measured is rotatably mounted, with a simple step even when a calibration tool is deformed due to secular change or the like.

BACKGROUND ART

Conventional X-ray measuring devices (measurement X-ray CT apparatus), which can measure a three-dimensional shape of an object to be measured with use of an X-ray, are mainly used for observation and inspection of defects, such as voids in casting parts, welding defects in welded parts, and defects in circuit patterns of electronic circuit parts, which are difficult to identify from external appearance. However, in recent years, with the spread of 3D printers, there are increasing demands for 3D measurement of internal dimensions of workpieces with higher accuracy. To meet these demands, the X-ray measuring devices are expected to further increase the accuracy of dimension measurement.

In order to perform more accurate dimension measurement in the X-ray measuring devices, it is important, as disclosed in Japanese Patent Application Laid-Open No. 2000-298105, to perform various calibration specific to each device, with use of a calibration tool prior to the start of measurement. Accordingly, it is desirable to constantly keep the calibration tool in a correct shape.

SUMMARY OF INVENTION

Technical Problem

However, there are cases where the calibration tool is deformed due to secular change or the like depending on management conditions. In such cases, when various calibration characteristic to each device is performed with the deformed calibration tool before the start of measurement, the measurement accuracy may deteriorate.

The present invention has been made in order to solve the above-described problems in the conventional technique, and an object thereof is to provide a calibration method of an X-ray measuring device, the method allowing calculation of, for example, a rotation center position of a rotating table on which an object to be measured is rotatably mounted, with a simple step even when a calibration tool is deformed due to secular change or the like.

Solution to Problem

In order to accomplish the above-stated object, a first aspect of the present invention provides a calibration method of an X-ray measuring device configured to measure a three-dimensional shape of an object to be measured using an X-ray. The X-ray measuring device includes an X-ray source that generates an X-ray, a rotating table on which the object to be measured is rotatably mounted, and an X-ray image detector that detects the X-ray passing through the object to be measured. The method includes: a mounting step of mounting on the rotating table a calibration tool that allows disposition of reference objects in N places (N≥4) at specific relative positional intervals, the reference objects having a shape that is identifiable by projected images on the X-ray image detector; a moving position acquisition step of parallelly moving a position of one reference object, out of two reference objects among the reference objects in the N places, with respect to a position of the other reference object without changing the specific relative positional intervals, irradiating the calibration tool with an X-ray, and acquiring from an output of the X-ray image detector a moving position that maximizes correlation between a projected image of the one reference object and a projected image of the other reference object; a relative position calculation step of performing the moving position acquisition step on the remaining reference objects so that all the reference objects in the N places are associated with each other on the basis of each of the moving positions, and calculating the specific relative positional intervals from each of the moving positions; a feature position calculation step of irradiating the calibration tool with an X-ray, and identifying positions of feature points of projected images of the reference objects in the N places from an output of the X-ray image detector; a transformation matrix calculation step of calculating a transformation matrix from the positions of the feature points of the projected images of the reference objects in the N places and the specific relative positional intervals, the transformation matrix being used for projective transformation of the reference objects onto a detection surface of the X-ray image detector; a rotation detection step of rotating the rotating table twice or more at a predetermined angle, and repeating execution of the feature position calculation step to the transformation matrix calculation step; a position calculation step of calculating absolute positions of the reference objects for each rotation at the predetermined angle on the basis of the transformation matrix; and a center position calculation step of calculating a rotation center position of the rotating table from change in the absolute positions of the reference objects caused by rotation of the rotating table.

A second aspect of the present invention provides the calibration method in which, in the moving position acquisition step, a differential position of the position of the feature point of the projected image of the one reference object with respect to the position of the feature point of the projected image of the other reference object may be calculated, and the reference objects in the N places may parallelly be moved on the basis of the differential position.

A third aspect of the present invention provides the calibration method in which, when the correlation between the projected image of the one reference object and the projected image of the other reference object is maximum, a magnitude of the differential position may be equal to or less than a specified value.

A fourth aspect of the present invention provides the calibration method in which, the rotating table may be rotated a plurality of times at a specific angle, the moving position acquisition step to the relative position calculation step may repeatedly be executed, and an average of the plurality of specific relative position intervals obtained by the repeated execution may be calculated, or positions before and after the parallel movement when the steps are repeatedly executed next time may be associated with the specific relative position intervals calculated immediately before.

A fifth aspect of the present invention provides the calibration method in which, when all the reference objects are mounted on only one plane in the calibration tool, the transformation matrix may be defined as a projective transformation matrix, and when the reference objects are mounted three-dimensionally, the transformation matrix may be defined as a projection matrix.

A sixth aspect of the present invention provides the calibration method in which, in the center position calculation step, a rotary axis of the rotating table may further be calculated.

A seventh aspect of the present invention provides the calibration method in which, in the position calculation step, on an assumption that the X-ray source and the X-ray image detector rotate instead of the rotating table, absolute positions of the reference objects may be calculated by calculating an absolute position of the X-ray source for each rotation at the predetermined angle on the basis of the transformation matrix and by transforming the absolute position of the X-ray source into coordinates.

An eighth aspect of the present invention provides the calibration method in which, when the absolute position of the X-ray source is calculated by rotating the rotating table three times or more at the predetermined angle, a distance between the X-ray source and the X-ray image detector and a position of a foot of a perpendicular from the X-ray source to the X-ray image detector may be converted into variables, and a distance error between a position on a locus of a provisional true circle and the absolute position of the X-ray source may be evaluated so as to calculate the distance between the X-ray source and the X-ray image detector and a position of the foot of the perpendicular from the X-ray source to the X-ray image detector, the provisional true circle being obtained by fitting the absolute positions of the X-ray source calculated on the basis of the transformation matrix to a true circle.

A ninth aspect of the present invention provides the calibration method in which, in the center position calculation step, a center position of a locus obtained by fitting change in the absolute positions of the reference objects to a true circle may be calculated, and the calculated center position may be defined as the rotation center position of the rotating table.

A tenth aspect of the present invention provides the calibration method in which, in calculation of the rotary axis of the rotating table, an angle of inclination from a horizontal plane of the locus may further be calculated, and the rotary axis may be calculated from the angle of inclination and the rotation center position.

An eleventh aspect of the present invention provides the calibration method in which, the reference objects may each be a sphere.

A twelfth aspect of the present invention provides the calibration method in which the positions of the feature points of the projected images of the reference objects may be centroid positions of the projected images.

Advantageous Effects of Invention

According to the present invention, it becomes possible to calculate, for example, a rotation center position of a rotating table, on which an object to be measured that is rotatably mounted, with a simple step, even when a calibration tool is deformed due to secular change or the like.

These and other novel features and advantages of the present invention will become apparent from the following detailed description of preferred embodiments.

BRIEF DESCRIPTION OF DRAWINGS

The preferred embodiments will be described with reference to the drawings, wherein like elements have been denoted throughout the figures with like reference numerals, and wherein.

DESCRIPTION OF EMBODIMENTS

Hereinafter, an embodiment of the present invention will be described in details with reference to the drawings. The present invention is not limited by the contents of the embodiment and examples described below. Moreover, component members described hereinbelow include those easily conceived by a person skilled in the art and those substantially identical, i.e., their full scope of equivalents. Furthermore, the component members disclosed hereinbelow can appropriately be combined or selected where necessary.

Figure 1:
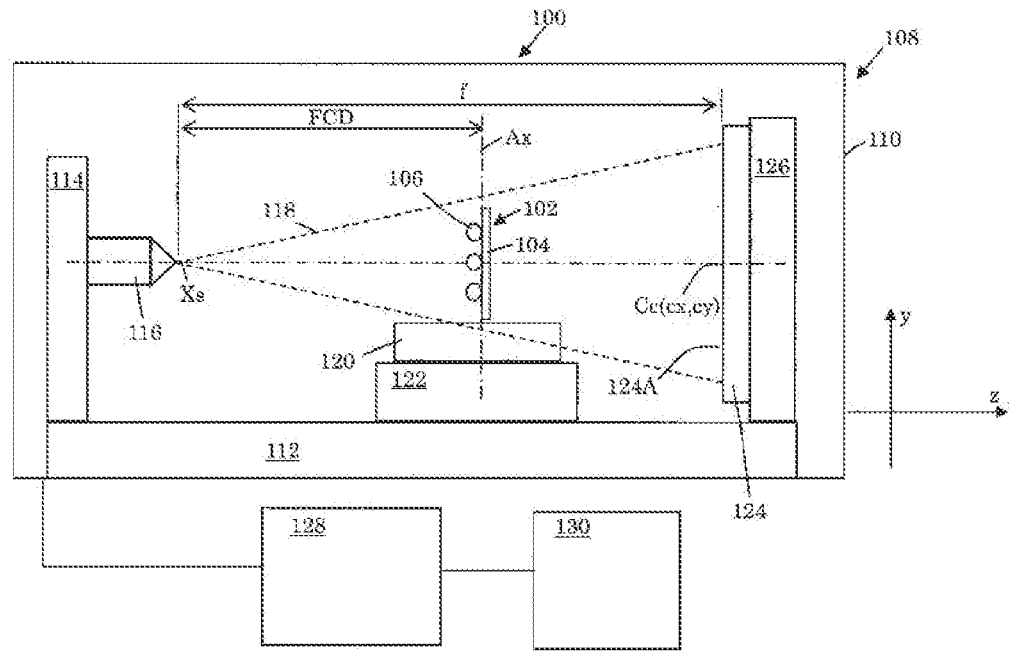
FIG. 1 is a schematic side view showing a basic configuration of an X-ray measuring device according to an embodiment of the present invention.

FIG. 1 shows an embodiment of the present invention. In FIG. 1, a description is given on the assumption that a width direction with respect to the page of FIG. 1 is a z-axis direction, a longitudinal direction with respect to the page is a y-axis direction, and a direction perpendicular to the page is an x-axis direction.

An X-ray measuring device 100 is a device for measuring a three-dimensional shape of an object to be measured with an X-ray. As shown in FIG. 1, the X-ray measuring device 100 includes a body unit 108, a host computer 128, and a motion controller 130.

Figure 2:
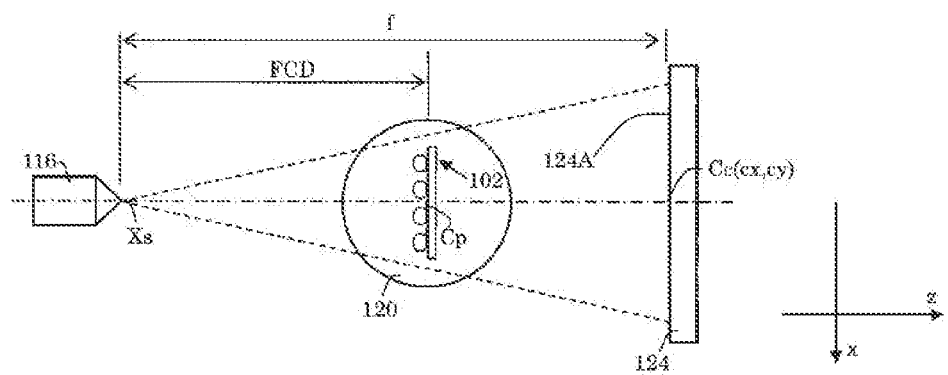
FIG. 2 is a schematic top view showing only essential parts of the X-ray measuring device of FIG. 1.
Figure 3A:
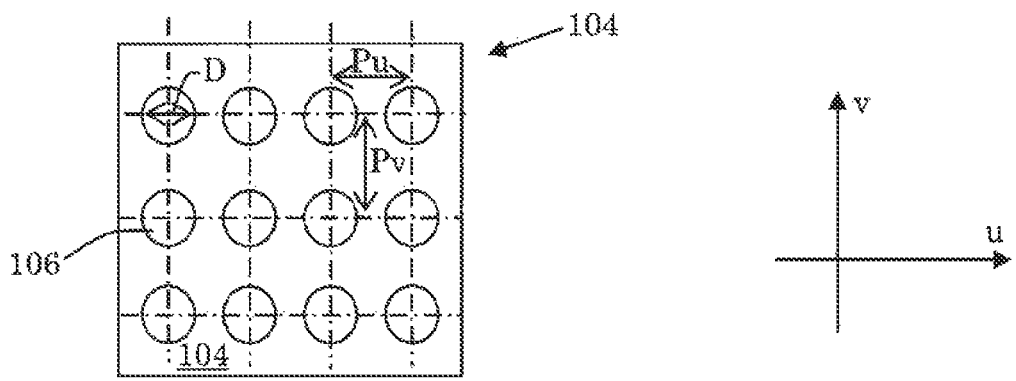
FIG. 3A is a front view showing a calibration tool of FIG. 1.
Figure 3B:
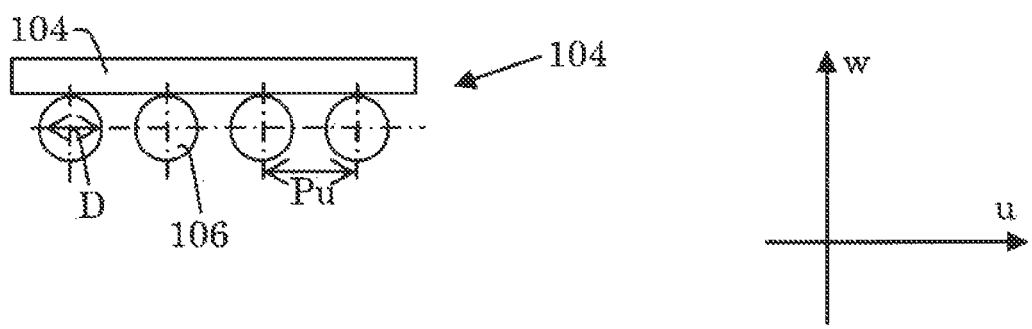
FIG. 3B is a top view showing the calibration tool of FIG. 1.

In FIGS. 1 and 2, a calibration tool 102 instead of an object to be measured is mounted on a rotating table 120. The calibration tool 102 is made of a material (for example, aluminum etc.) which can transmit an X-ray 118 as shown in FIG. 3A and FIG. 3B. It is assumed that the calibration tool 102 is used to include a plurality of (for example, the number (N) is 4*3=12) spheres (reference objects) 106 having a diameter D provided at fixed relative positional intervals on a planar member 104 (i.e., the spheres 106 are disposed in N places at relative positional intervals (which are also referred to as relative positions)). However, although the fixed relative positional intervals are used to be known, it is assumed that the calibration tool 102 has deformed due to secular change, and the positions of all the spheres 106 are now shifted from the fixed relative positional intervals (i.e., in FIGS. 3A and 3B, specific relative positional intervals Pu, Pv are unknown and are no longer fixed). At this point of time, it can be said that the relative positions X(1 to N) of the N spheres 106, in other words, the spheres 106 in N places, are unknown (relative positions X(1 to N) are identical to X1 to XN; this applies in the description below). However, in the present embodiment, it is assumed that all the spheres 106 are mounted on only one plane in the calibration tool 102. The spheres 106 have a simple shape which can easily be identified by their projected images onto an X-ray image detector 124. In FIG. 3A, a width direction with respect to the page of FIG. 1 is a u-axis direction, a longitudinal direction with respect to the page is a v-axis direction, and a direction perpendicular to the page is a w-axis direction.

The calibration tool 102 includes a triaxial linear motion stage which moves the planar member 104 in the direction of three axes x, y, and z. Accordingly, the calibration tool 102 can freely perform parallel movement of the spheres 106 disposed in N places without changing the specific relative positional intervals of the spheres 106 each other (without being limited thereto, the rotating table 120 may include the triaxial linear motion stage). The position of the rotating table 120 when the calibration tool 102 is mounted on the rotating table 120 and is irradiated with an X-ray 118, but the triaxial linear motion stage does not yet move, is defined as a first table position Dis1. Then, the position of the rotating table 120 when the X-ray 118 is emitted and the triaxial linear motion stage moves for an i(1≤i≤N)-th time, so that a differential position Erj in a later-described expression (1) satisfies a later-described expression (2) when i=j, is defined as an i-th table position Disi.

As shown in FIG. 1, the body unit 108 includes, on the base 112, an X-ray shielding cover 110 to prevent leakage of the X-ray 118, an X-ray source 116 to generate the X-ray 118, the rotating table 120 on which an object to be measured (not illustrated) is rotatably mounted, and the X-ray image detector 124 to detect the X-ray 118 that passes through the object to be measured. The X-ray source 116 is provided on an X-ray source support stand 114 on the base 112. The X-ray source support stand 114 can include a linear motion mechanism which can move the X-ray source 116 in three axial directions of x, y, and z. The rotating table 120 is provided on a table support stand 122 on the base 112. The table support stand 122 includes a linear motion mechanism which can move the object to be measured in three axial directions of x, y, and z. The table support stand 122 may further be provided with an inclination mechanism which can adjust inclination of a rotary axis Ax of the rotating table 120. The X-ray image detector 124 has a two-dimensional detection surface 124A that is sensitive to the X-ray 118. The X-ray image detector 124 is supported by a detector support stand 126 on the base 112. The detector support stand 126 may also include a linear motion mechanism which can move the X-ray image detector 124 in three axial directions of x, y, and z. A radiation beam of the X-ray 118 from the X-ray source 116 conically spreads in the z-axis direction, with its center line being adjusted so as to be orthogonal to the rotary axis Ax of the rotating table 120 and constitute a perpendicular of the detection surface 124A of the X-ray image detector 124.

The host computer 128 shown in FIG. 1 controls the X-ray source support stand 114, the X-ray source 116, the rotating table 120, the table support stand 122, the X-ray image detector 124, and the detector support stand 126 of the body unit 108. The host computer 128 can also read and execute programs stored in a storage unit, which is not illustrated, to perform automatic or semiautomatic measuring operation and calibration of the X-ray measuring device 100. In other words, in the measuring operation of the X-ray measuring device 100, the host computer 128 reconstructs, for example, data on the projected images obtained by the X-ray image detector 124, and creates three-dimensional volume data on the object to be measured.

In calibration of the X-ray measuring device 100, the host computer 128 calculates, as expressed by the expression (1) for example, a differential position Erj that is a difference of a centroid position $ImDisj_h\_Sphr\_j$ ($2 \le j \le N$) of the projected image of the j-th (one) sphere 106 out of the two spheres 106, with respect a centroid position ImDis1_Sphr_1 of the projected image of a first (the other) sphere 106:

$$Erj = ImDis1\_Sphr\_1 - ImDisj_h\_Sphr\_j \quad (1)$$

A reference sign $Disj_h$ denotes a table position when the spheres 106 are parallelly moved until the j-th table position Disj is obtained. Specifically, when the table position $Disj_h$ becomes equal to the table position Disj, the expression (2) is satisfied. Accordingly, in that case, the host computer 128 is configured to determine that the correlation between the projected image of the first sphere 106 and the projected image of the j-th sphere 106 becomes maximum. Note that a specified value Vx is a value closer to zero than the accuracy of calibration, and can properly be determined in accordance with an accuracy level of calibration.

$$Erj \le Vx \quad (2)$$

A moving position Mj of the j-th sphere 106 with respect to the first sphere 106 in this case is expressed by an expression (3):

$$Mj = Dis1 - Disj \quad (3)$$

In short, a relative position Xj of the j-th sphere 106 with respect to the first sphere 106 is expressed by an expression (4):

$$Xj = Mj = Dis1 - Disj \quad (4)$$

That is, in the present embodiment, the table positions Dis(1 to N) are defined as relative positions X(1 to N) of the spheres 106, respectively.

Figure 7A:
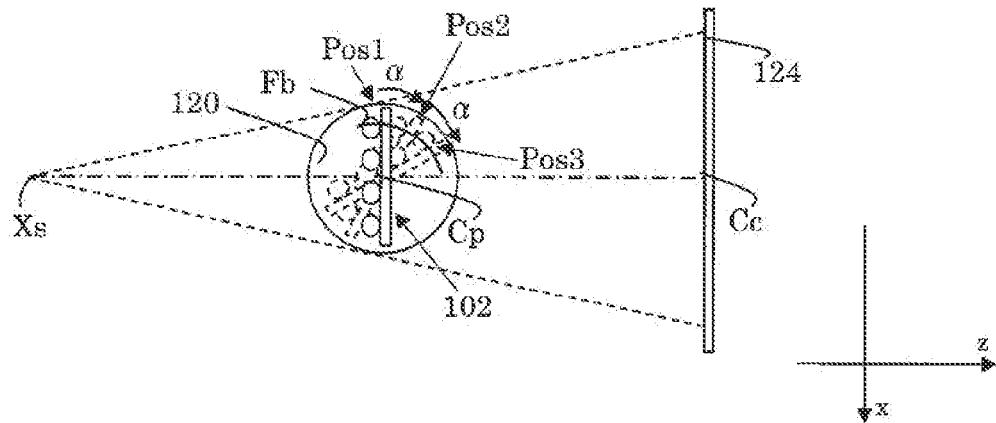
FIG. 7A shows the relationship between the absolute positions of the spheres and the absolute position of the X-ray source, in which the rotating table rotates.
Figure 7B:
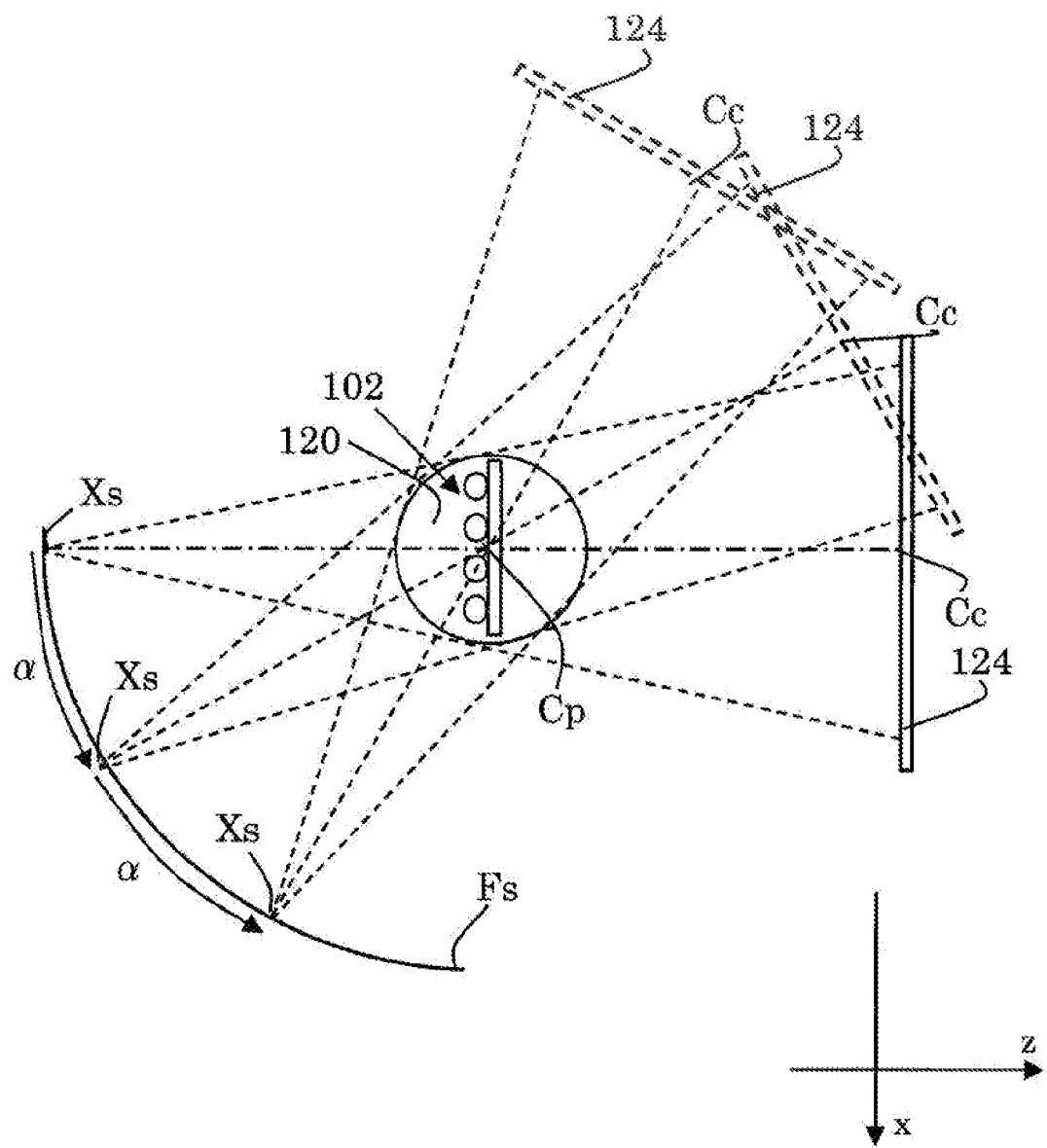
FIG. 7B shows the relationship between the absolute positions of the spheres and the absolute position of the X-ray source, in which the X-ray source and the X-ray image detector are assumed to rotate.

For example, on the assumption that instead of the rotating table 120, the X-ray source 116 rotates based on a projective transformation matrix (transformation matrix) Hk made of 3 rows*3 columns in a k(1≤k≤Q; Q is a natural number of 3 or more)-th rotational position of the rotating table 120, the host computer 128 can calculate, with use of the relationship expressed by a series of expressions shown below, an absolute position Xs of the X-ray source 116 in the k-th assumed rotational position (FIGS. 7A and 7B).

Specifically, first of all, an internal parameter matrix A expressed by an expression (5) is defined from a distance f between the X-ray source 116 and the X-ray image detector 124, and a position Cc (cx, cy) of a foot of a perpendicular from the X-ray source 116 to the X-ray image detector 124.

When an aspect ratio of pixels in the X-ray image detector 124 differs, the distance f in the first row first column and the distance f in the second row second column in the internal parameter matrix A are slightly different in value from each other. While a skew S related to distortion of an image may be used for the first row second column in the internal parameter matrix A, the skew S is set to zero in the present embodiment.

$$A = \begin{bmatrix} f & 0 & cx \\ 0 & f & cy \\ 0 & 0 & 1 \end{bmatrix} \quad (5)$$

In this case, a rotation matrix Rk in the k-th assumed rotational position is made of 3 rows*3 columns which are constituted of three column vectors rk1, rk2, and rk3. The rotation matrix Rk can be expressed by an expression (6):

$$Rk=[rk1\,rk2\,rk3] \quad (6)$$

Here, the projective transformation matrix Hk can be decomposed as in an expression (7) by using a translation matrix Tk in the k-th assumed rotational position (translation vectors of one column), and the expressions (5) and (6).

$$Hk=[rk1\,rk2\,Tk] \quad (7)$$

From the expression (7), the absolute position Xs of the X-ray source 116 in the k-th assumed rotational position can be calculated as expressed in an expression (8). Note that a reference sign −inv( ) denotes an inverse matrix.

$$Xs=-inv(Rk)*Tk \quad (8)$$

The host computer 128 can also calculate the absolute positions Xa(1 to N) of the spheres 106 in a k-th rotational position Posk by performing coordinate transformation of the absolute position Xs of the X-ray source 116 in the k-th assumed rotational position.

The host computer 128 can also calculate the rotation center position Cp of the rotating table 120 from change in the absolute positions Xa(1 to N) of the spheres 106 caused by rotation of the rotating table 120.

When the distance f between the X-ray source 116 and the X-ray image detector 124 and the position Cc of the foot of the perpendicular from the X-ray source 116 to the X-ray image detector 124 are unknown, the host computer 128 converts the distance f and the position Cc into variables, substitutes appropriate values into the variables, and calculates the absolute positions Xs of the X-ray source 116 in Q places by using the expression (8), that is, on the basis of the projective transformation matrix Hk (k=1 to Q). The host computer 128 fits the calculated absolute positions Xs of the X-ray source 116 in the Q places to a true circle (provisional true circle) by, for example, a least square method. The host computer 128 then evaluates a distance error between the positions on a locus of the provisional true circle and the absolute positions Xs of the X-ray source 116 in the Q places, and calculates the distance f and the position Cc having the least distance error. In this case, the total number Q of the rotational positions is three or more, that is, the rotating table 120 is rotated three times or more at a predetermined angle α.

The motion controller 130 shown in FIG. 1, which is connected to the host computer 128, controls the X-ray source 116, rotation and movement of the rotating table 120, and various mechanisms of the body unit 108.

Next, the measuring operation of the X-ray measuring device 100 will briefly be described.

In measuring operation, the object to be measured is rotated on the rotating table 120 in the state where the X-ray 118 is generated, and projected images are collected from a plurality of angular directions (the number of angle divisions being, for example, about 1000 to 6000). The collected projected images are subjected to reconstruction processing with a slice surface horizontally crossing the object to be measured as a datum level, so as to create three-dimensional volume data (three-dimensional images) of the object to be measured.

Next, the calibration procedure of the X-ray measuring device 100 will be described with reference to FIGS. 4 to 6. Here, the host computer 128 performs all the arithmetic calculation processes. Note that, for example, when i=1, the i-th table position Disi represents the table position Dis1. Centroid positions ImDis(1 to N)_Sphr_(1 to N) represent centroid positions ImDis1_Sphr_1 to ImDisN_Sphr_N. When k=1, the k-th rotational position Posk represents a rotational position Pos1. When the number of the spheres 106 is N in the k-th rotational position Posk, the centroid positions ImPosk_Sphr_(1 to N) represent centroid positions ImPosk_Sphr_1 to ImPosk_Sphr_N of N spheres 106 in the k-th rotational position Posk.

Figure 4:
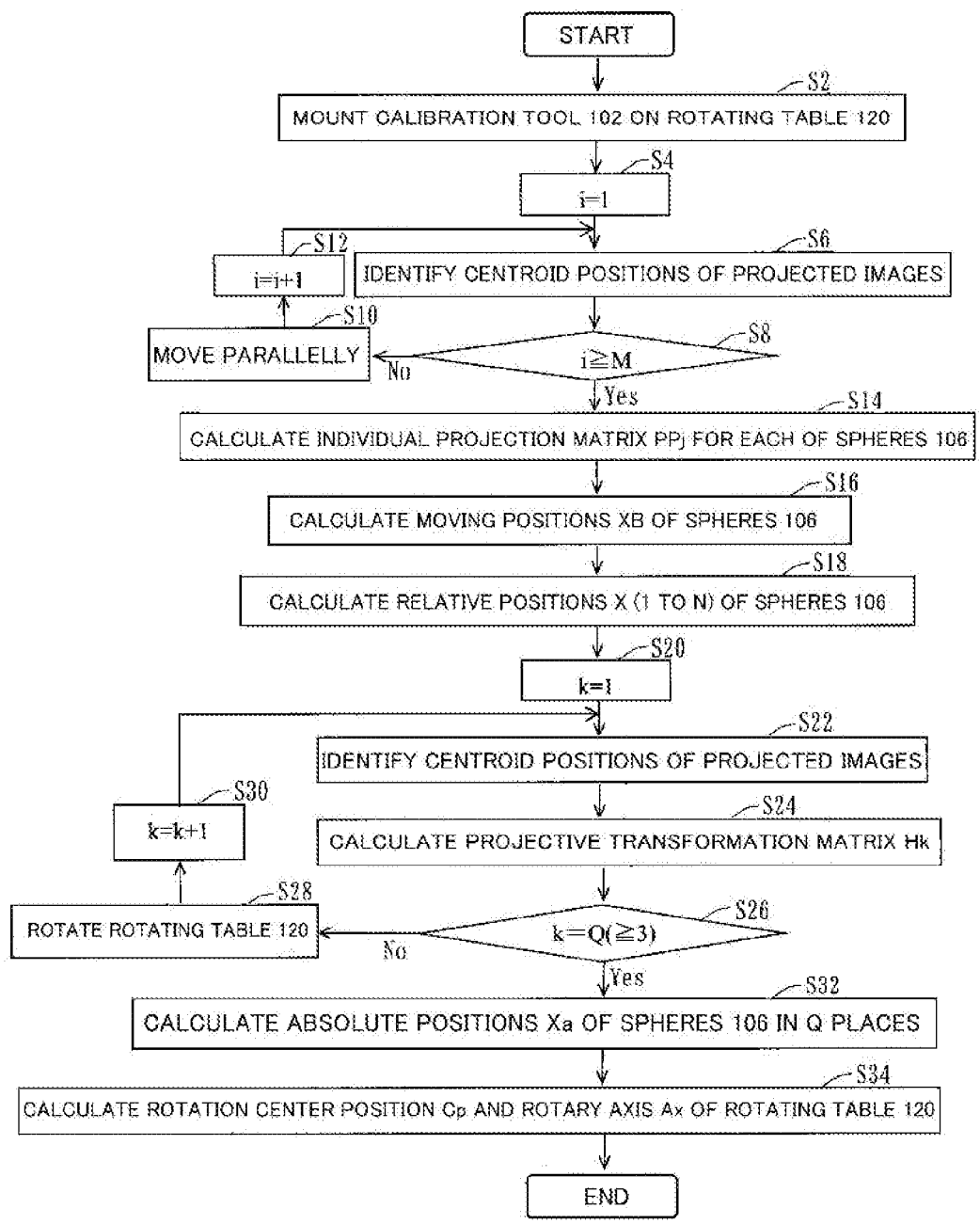
FIG. 4 is a flowchart showing calibration procedures of the X-ray measuring device according to the embodiment of the present invention.

First, the calibration tool 102 including the plurality of spheres 106 at specific relative positional intervals is mounted on the rotating table 120 (step S2 of FIG. 4; mounting step).

Next, when j=2 is set, the position of the j-th sphere 106, out of two spheres 106 among the spheres 106 in N places, is parallelly moved with respect to the position of the first sphere 106, without changing the specific relative positional intervals of the spheres 106 in the N places. At this time, the calibration tool 102 is irradiated with the X-ray 118. Accordingly, from an output of the X-ray image detector 124, a moving position Mj where the magnitude of the differential position Erj of the centroid position ImDisj$_h$_Sphr_j of a projected image of the j-th sphere 106 with respect to the centroid position ImDis1_Sphr_1 of the projected image of the first sphere 106 becomes equal to or less than the specified value Vx is acquired (moving position acquisition step). This step is mainly performed in step S4 to step S12 of FIG. 4 described below.

First, the calibration tool 102 is irradiated with the X-ray 118 while the spheres 106 are not parallelly moved. From an output of the X-ray image detector 124, the centroid positions (positions of feature points) ImDis1_Sphr (1 to N) of the projected images of N (N=12) spheres 106 are identified and recorded, respectively (step S4 of FIG. 4). Then, for the second sphere 106, j=2 is set (step S6 of FIG. 4).

Next, the differential position Erj of the centroid position ImDisj$_h$_Sphr_j of the projected image of the j-th sphere 106 with respect to the centroid position ImDis1_Sphr_1 of the projected image of the first sphere 106 is calculated. On the basis of the differential position Erj, the spheres 106 in the N places are parallelly moved (step S8 of FIG. 4). In this case, as the moving position Mj which prescribes the parallel movement, the differential position Erj can be used without change.

Next, the calibration tool 102 is irradiated with the X-ray 118 again. From the output of the X-ray image detector 124, the centroid position ImDisj$_h$_Sphr_j of the projected image of the j-th sphere 106 is identified (step S10 of FIG. 4). Here, the table position Disj$_h$ can be a position obtained by adding the first table position Dis1 to the moving position Mj. Then, the differential position Erj of the centroid position ImDis- $j_n$_Sphr_j of the projected image of the j-th sphere 106 with respect to the centroid position ImDis1_Sphr_1 of the projected image of the first sphere 106 is calculated.

Next, it is determined whether the differential position Erj is equal to or less than the specified value Vx (step S12 of FIG. 4). When the differential position Erj is not equal to or less than the specified value Vx (No in step S12 of FIG. 4), the process from step S8 to step S12 is repeated until the differential position Erj becomes equal to or less than the specified value Vx. The moving position Mj which prescribes next parallel movement may be determined by comparing, for example, the magnitude of the previous (first) differential position Er1 and the magnitude of the present differential position Er2.

Once the differential position Erj becomes equal to or less than the specified value Vx (Yes in step S12 of FIG. 4), the moving position Mj is recorded.

Next, the moving position acquisition step is performed on all the remaining spheres 106 in the N places so that all the spheres 106 are associated with each other on the basis of the moving position Mj, and the relative positions (specific relative positional intervals) X (1 to N) of the spheres 106 are calculated from the respective moving positions Mj (j=1 to N) (relative position calculation step). This step is mainly constituted of step S14 to step S18 of FIG. 4 described below.

Since the moving position Mj (j=2) of the j-th sphere 106 with respect to the first sphere 106 has been acquired first, the moving positions Mj (j=3 to N) of the j=3rd to N-th spheres 106 with respect to the first sphere are acquired in step S14 and step S16. Once the moving positions Mj (j=2 to N) of the j-th spheres 106 with respect to the first sphere 106 are acquired (Yes in step S14 of FIG. 4), the process proceeds to step S18 of FIG. 4. In the present embodiment, based on the first sphere 106, the moving position acquisition step is performed on the remaining spheres 106 by aligning the positions of the remaining spheres 106 with the position of the first sphere 106, so that all the spheres 106 in N places are associated with each other on the basis of the moving position Mj (without being limited thereto, the position of a j+1st sphere 106 may be aligned with the position of the j-th sphere 106, for example).

Next, the relative positions X(1 to N) of the spheres 106 are calculated by using the moving positions Mj (j=2 to N) of the j=second to N-th spheres 106 with respect to the first sphere 106 (step S18 of FIG. 4).

Next, the state where the rotating table 120 does not yet rotate is set to k=1 (step S20 of FIG. 4). Then, the calibration tool 102 is irradiated with the X-ray 118. From the output of X-ray image detector 124, the centroid positions ImPosk-_Sphr_(1 to N) of the projected images of the spheres 106 in the N places are identified, respectively (step S22 of FIG. 4; feature position calculation step). For this step, the result of executing step S4 of FIG. 4 may be used.

Next, from the centroid positions ImDis(1 to N)_Sphr (1 to N) of the projected images of the spheres 106 in the N places and the relative positions X(1 to N) of the spheres 106, a projective transformation matrix Hk used for projective transformation of the spheres 106 to the detection surface 124A of the X-ray image detector 124 is calculated (step S24 of FIG. 4; transformation matrix calculation step).

Next, it is determined whether the number k of the rotational positions Posk is equal to or more than Q (the number k may be three or more in the present embodiment) (step S26 of FIG. 4). When the number k of the rotational positions Posk is not equal to or more than Q (Q≥3) (No in step S26 of FIG. 4), the rotating table 120 is rotated at a predetermined angle α (step S28 of FIG. 4). Then, the number k of the rotational positions Posk is incremented by 1 (step S30 of FIG. 4), and step S22 and step S24 are repeated (step S22 to step S30; rotation detection step). When the number k of the rotational positions Posk becomes equal to or more than Q (Q 3) (Yes in step S26 of FIG. 4), the process proceeds to step S32. In other words, in the rotation detection step, the rotating table 120 is rotated twice or more at the predetermined angle α, and execution of the feature position calculation step to the transformation matrix calculation step is repeated. In the present embodiment, although the predetermined angle α is fixed to, for example, 30 degrees, the angle is not limited in particular. The predetermined angle α may be a smaller angle, or take a different value every time.

Next, on the basis of the projective transformation matrix Hk (k=1 to Q), absolute positions Xa(1 to N) of the spheres 106 (Q places) for each rotation at the predetermined angle α are calculated (step S32 of FIG. 4; position calculation step). The detail of the step will also be described later.

Next, from change in absolute positions Xa(1 to N) of the spheres 106 in Q places caused by rotation of the rotating table 120, the rotation center position Cp and the rotary axis Ax of the rotating table 120 are calculated (step S34 of FIG. 4; center position calculation step). In this step, first, a center position Cp of a locus Fb, obtained by fitting each of the change in the absolute positions Xa(1 to N) of the spheres 106 to a true circle, is calculated, and the obtained center position Cp is set as the rotation center position Cp of the rotating table 120. More specifically, the absolute positions Xa(1 to N) of the spheres 106 in the Q places are each fitted to a true circle. If Q>3 at the time, the center position Cp of the true circle is calculated by, for example, the least square method. If Q=3, the center position Cp of the true circle is calculated by, for example, a simultaneous equation.

Then, for instance, an angle of inclination from a horizontal plane (xz plane) of the locus Fb obtained by fitting to a true circle is calculated. Then, the rotation center position Cp and the rotary axis Ax of the rotating table 120 are calculated. In this case, in each of 12 (N=12) spheres 106, the center position Cp of the true circle and its locus Fb are calculated. Accordingly, the rotation center position Cp can be calculated by equalizing the center positions Cp of the true circles of the twelve spheres 106, and the angle of inclination of the rotary axis Ax can be calculated by equalizing the values of the inclination from the horizontal plane of the loci Eb of these true circles. As a result, the rotary axis Ax can be calculated.

Here, one example of the position calculation step will be described with reference to FIG. 5.

Figure 5:
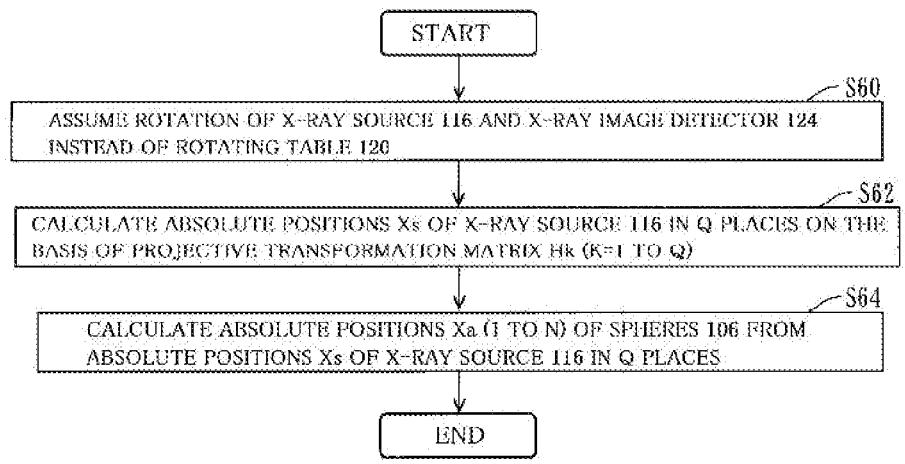
FIG. 5 is a detailed flowchart of a step of calculating absolute positions of spheres from an absolute position of an X-ray source in FIG. 4.

First, assume that instead of the rotating table 120, the X-ray source 116 and the X-ray image detector 124 rotate (step S60 of FIG. 5). Incidentally, the predetermined angle α and the locus Fb of the sphere 106 when the rotating table 120 rotates are shown in FIG. 7A. A locus Fs of the absolute positions Xs of the X-ray source 116 when it is assumed that the X-ray source 116 and X-ray image detector 124 rotate is described in FIG. 7B.

Next, on the basis of the projective transformation matrix Hk (k=1 to Q), the absolute positions Xs of the X-ray source 116 for each rotation at the predetermined angle α, that is, in Q places are calculated (step S62 of FIG. 5).

Next, the absolute positions Xa(1 to N) of the spheres 106 in Q places are calculated by coordinate transformation of the absolute positions Xs of the X-ray source 116 in Q places (step S64 of FIG. 5).

There is a case where, when the absolute positions Xs of the X-ray source 116 in Q places are calculated in the above-described position calculation step, the distance f between the X-ray source 116 and the X-ray image detector 124 and the position Cc of the foot of the perpendicular from the X-ray source 116 to the X-ray image detector 124 are unknown. The case will be described below with reference to FIG. 6.

Figure 6:
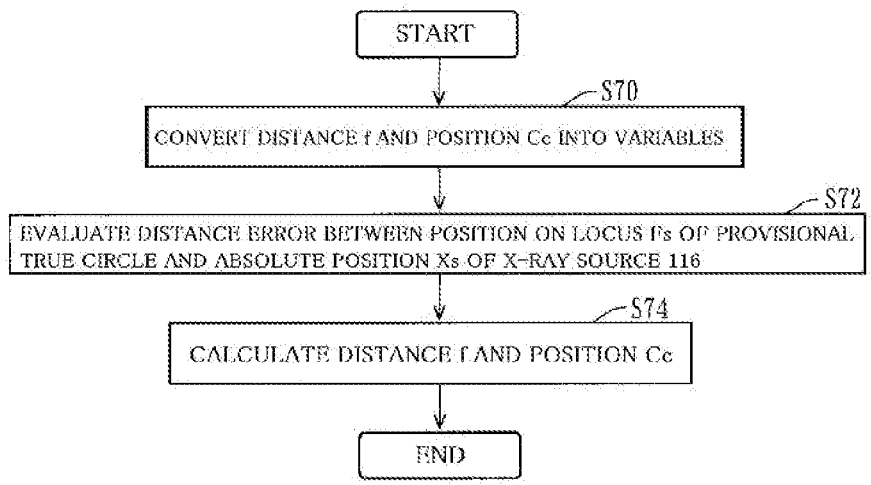
FIG. 6 is a flowchart for calculating a distance between the X-ray source and the X-ray image detector, and a position of a foot of a perpendicular from the X-ray source to the X-ray image detector, after calculating the absolute position of the X-ray source in FIG. 5.

First, when the absolute position Xs of the X-ray source 116 in the k-th assumed rotational position is calculated, the distance f between the X-ray source 116 and the X-ray image detector 124, and the position Cc of the foot of the perpendicular from the X-ray source 116 to the X-ray image detector 124 are converted into variables (step S70 of FIG. 6). Then, a distance error between a position on a locus Fs of a provisional true circle, obtained by fitting the absolute positions Xs of the X-ray source 116 to a true circle, in the k-th assumed rotational position calculated on the basis of the projective transformation matrix Hk, and the absolute position Xs of the X-ray source 116 is evaluated (step S72 of FIG. 6). Then, the distance f and the position Cc which minimize the distance error are calculated (step S74 of FIG. 6).

Specifically, for example, the distance f is temporarily set to an appropriate value, and the position Cc is made to vary. In this process, the position Cc which minimizes the distance error is calculated. Next, the position Cc is temporarily set to the value which minimizes the distance error, and this time, the distance f is made to vary. In this process, the distance f which minimizes the distance error is calculated. The distance f is temporarily set to the value which minimizes the distance error, and the position Cc is made to vary. In this process, the position Cc which minimizes the distance error is calculated. The position Cc is temporarily set to the value which minimizes the distance error, and the distance f is made to vary again. In this process, the distance f which minimizes the distance error is calculated. By repeating this process several times, it is possible to calculate the distance f and the position Cc which can minimize the distance error, and therefore the distance f and the position Cc can be optimized.

Thus, in the present embodiment, the calibration tool 102 including N spheres 106 at specific relative positional intervals (unknown intervals) is first mounted on the rotating table 120. Then, the position of the j-th sphere 106, out of two spheres 106 among N spheres 106, is parallelly moved with respect the position of the first sphere 106, without changing the specific relative positional intervals. Then, the moving position Mj where the magnitude of the differential position Erj of the centroid position $ImDisj_h\_Sphr\_j$ of a projected image of the j-th sphere 106 with respect to the centroid position ImDis1_Sphr_1 of the projected image of the first sphere 106 becomes equal to or less than the specified value Vx is acquired. Then, all the spheres 106 in the N places are associated each other on the basis of the moving positions Mj, and the specific relative positional intervals are calculated from each of the moving positions Mj. Then, the rotating table 120 is set to three rotation angles, where projected images of the calibration tool 102 are acquired. In short, in the present embodiment, the rotation center position Cp of the rotating table 120 can be calculated with a series of very simple steps. Moreover, the specific relative positional intervals can be obtained in the step of, so to speak, laying the position of the projected image of the j-th sphere 106 on top of the position of the projected image of the first sphere 106. This makes it unnecessary to perform complicated arithmetic processes to obtain the specific relative positional intervals. Furthermore, in the present embodiment, it is not necessary to create three-dimensional volume data to calculate the rotation center position Cp. Therefore, calibration can be conducted by simple processes.

In the present embodiment, in the moving position acquisition step, the differential position Erj of the centroid position $ImDisj_h\_Sphr\_j$ of the projected image of the j-th sphere 106 with respect to the centroid position ImDis1_Sphr_1 that is the feature point of the projected image of the first sphere 106 is calculated. The spheres 106 in N places are parallelly moved in consideration of a projecting magnification of the projected images on the basis of the calculated differential position Erj. Accordingly, the arithmetic calculation for calculating the differential position Erj is facilitated, and the moving positions Mj which prescribe parallel movement of the spheres 106 in the N places can swiftly be calculated. This makes it possible to implement swift parallel movement.

In the present embodiment, in the case where the correlation between the projected image of the first sphere 106 and the projected image of the j-th sphere 106 becomes maximum, the magnitude of the differential position Erj becomes equal to or less than the specified value Vx. Accordingly, the arithmetic calculation itself can be performed more simply than actual correlation calculation, and the process to obtain the maximum correlation can be reduced. As a result, faster calibration can be achieved. The present invention is not limited to the foregoing configuration. The magnitude of the differential position Erj may be zero, and individual actual correlation may be calculated by arithmetic processing.

In the present embodiment, since all the spheres 106 are mounted on only one plane in the calibration tool 102, the projective transformation matrix Hk is used as the transformation matrix for projective transformation of the spheres 106 in the k-th rotational position Posk to the detection surface 124A of the X-ray image detector 124. Accordingly, the rotation center position Cp of the rotating table 120 can be calculated by using, as calculation targets, only four spheres 106, out of 12 spheres 106. This allows further reduction in calibration time. In the present embodiment, the rotation center position Cp of the rotating table 120 can be calculated extremely accurately by using not only the four spheres 106 but all the 12 spheres 106 as the targets of arithmetic calculation in each step.

In the present embodiment, the rotary axis Ax of the rotating table 120 is further calculated in the center position calculation step. Accordingly, even in the case where calibration of the rotary axis Ax of the rotating table 120 is first assumed to be unnecessary, it is possible to properly evaluate the necessity for calibration by comparing the rotary axis Ax with the result of actual calculation of the rotary axis Ax of the rotating table 120.

In the present embodiment, it is assumed in the position calculation step that the X-ray source 116 and the X-ray image detector 124 rotate instead of the rotating table 120. On this assumption, the absolute position Xs of the X-ray source 116 for each rotation at the predetermined angle α is calculated from the projective transformation matrix Hk, and the absolute positions Xa of the spheres 106 are calculated by performing coordinate transformation of the absolute position Xs of the X-ray source 116. In other words, instead of directly calculating the absolute positions Xa of the spheres 106, the absolute position Xs of the X-ray source 116 is calculated first. Consequently, the projective transformation matrix Hk is directly used. As a result, the calculation amount can be reduced, and swift calibration can be achieved. The present invention is not limited to this configuration. Instead, a method of directly calculating the absolute positions Xa of the spheres 106 may be used.

In the present embodiment, when the rotating table 120 is rotated three times or more at the predetermined angle α to calculate the absolute positions Xs of the X-ray source 116 in Q places, the distance f between the X-ray source 116 and the X-ray image detector 124 and the position Cc of the foot of the perpendicular from the X-ray source 116 to the X-ray image detector 124 are converted into variables. Then, a distance error between the position on the locus Fs of a provisional true circle, obtained by fitting the absolute positions Xs of the X-ray source 116 in Q places calculated on the basis of the projective transformation matrix Hk (k=1 to Q) to a true circle, and the absolute position Xs of the X-ray source 116 in the Q places is evaluated. On the basis of the evaluation of the distance error, the distance f between the X-ray source 116 and the X-ray image detector 124 and the position Cc of the foot of the perpendicular from the X-ray source 116 to the X-ray image detector 124 are calculated. Therefore, in the case of calibrating the distance f between the X-ray source 116 and the X-ray image detector 124 and the position Cc of the foot of the perpendicular from the X-ray source 116 to the X-ray image detector 124, these values can be calculated, and more accurate calibration can be performed.

In the present embodiment, in the center position calculation step, the center position Cp of the locus Fb, obtained by fitting each of the changing absolute positions Xa(1 to N) of the spheres 106 to a true circle, is calculated, and the obtained center position Cp is set as the rotation center position Cp of the rotating table 120. In other words, by fitting the absolute positions to a true circle, the total number Q of rotational positions can be reduced, and the center position Cp can uniquely be calculated. However, the present invention is not limited to this configuration. The rotation center position Cp of the rotating table 120 may be calculated by other methods.

In the present embodiment, in the case of calculating the rotary axis Ax of the rotating table 120, the angle of inclination from the horizontal plane of the locus Fb obtained by fitting to a true circle is calculated, and the rotary axis Ax is calculated from the angle of inclination and the rotation center position Cp. Accordingly, the rotary axis Ax can be calculated with only one sphere 106. This makes it possible to simplify the step of calculating the rotary axis Ax and to perform the step in a short time. However, the present invention is not limited to this. For example, the locus Fb obtained by fitting to a true circle is calculated in each of the spheres 106, and the rotary axis Ax may be calculated on the basis of a shift from each of the center positions Cp.

In the present embodiment, the reference objects on the calibration tool 102 are the spheres 106. Accordingly, outlines of the spheres 106 are circular (including the case of being ellipsoidal) whichever direction their images are projected. It means that the spheres 106 have a shape, as a reference object, most easily identifiable by their images projected to the X-ray image detector 124. However, the present invention is not limited to this. The reference objects may be, for example, a polyhedron including a regular polyhedron and a deformed rhomb, and may have shapes including curved surfaces, such as an ellipsoid and a cone.

In the present embodiment, the positions of the feature points of the projected images of the spheres 106 that are reference objects are the centroid positions of the projected images. Since the projected images of the spheres 106 are circular, it is easy to calculate their centroid positions, and it is possible to calculate with less position error. However, the present invention is not limited to this configuration. The positions of the feature points of the projected images of the spheres 106 that are reference objects may be their center positions. Alternatively, when the reference objects are not spheres, but locally include characteristic recess portions or protruding portions, the characteristic recess portions and protruding portions are associated with the feature points of the projected images.

Specifically, in the present invention, it is possible to easily calculate the rotation center position Cp of the rotating table 120, on which an object to be measured is rotatably mounted, with a simple step, even when the calibration tool 102 is deformed due to secular change or the like.

In the foregoing embodiment, all the spheres 106 are mounted on only one plane in the calibration tool 102. However, the present invention is not limited to this. For example, the spheres 106 may be mounted on the calibration tool 102 three-dimensionally, instead of all the spheres 106 being mounted on one plane. In that case, a projection matrix Pk is used instead of the projective transformation matrix Hk. Instead of the expression (7), the host computer 128 can use an expression (9) related to the projection matrix Pk below to calculate the absolute position Xs of the X-ray source 116 from the projection matrix Pk made of 3 rows*4 columns in the k-th assumed rotational position.

$$Pk=A[rk1\,rk2\,rk3\,Tk] \quad (9)$$

In this case, even if the plane accuracy of the calibration tool 102 is not good, accurate calibration can be performed by using the projection matrix Pk.

Although N is 12 in the foregoing embodiment, the present invention is not limited to this. For example, the calibration tool 102 may be configured such that there is one sphere 106 and the one sphere 106 is moved to and disposed in at least four places (N≥4).

The present invention is widely applicable to calibration of the X-ray measuring devices.

It should be apparent to those skilled in the art that the above-described embodiments are merely illustrative which represent the application of the principles of the present invention. Numerous and varied other arrangements can be readily devised by those skilled in the art without departing from the spirit and the scope of the present invention.

The invention claimed is:

1. A calibration method of an X-ray measuring device configured to measure a three-dimensional shape of an object to be measured using an X-ray, the X-ray measuring device including an X-ray source that generates the X-ray, a rotating table on which the object to be measured is rotatably mounted, and an X-ray image detector that detects the X-ray passing through the object to be measured, the method comprising:

mounting on the rotating table a calibration tool that allows disposition of reference objects in N places (N≥4) at specific relative positional intervals, the reference objects having a shape that is identifiable by projected images on the X-ray image detector;

parallelly moving a position of one reference object, out of two reference objects among the reference objects in the N places, with respect to a position of the other reference object without changing the specific relative positional intervals, irradiating the calibration tool with the X-ray, and acquiring from an output of the X-ray image detector a moving position that maximizes correlation between a projected image of the one reference object and a projected image of the other reference object;

performing the parallelly moving of the reference objects disposed in the N places on the remaining reference objects so that all the reference objects in the N places are associated with each other on a basis of each of the moving positions, and calculating the specific relative positional intervals from each of the moving positions;

irradiating the calibration tool with the X-ray, and identifying positions of feature points of projected images of the reference objects in the N places from an output of the X-ray image detector;

calculating a transformation matrix from the positions of the feature points of the projected images of the reference objects in the N places and the specific relative positional intervals, the transformation matrix being used for projective transformation of the reference objects onto a detection surface of the X-ray image detector;

rotating the rotating table twice or more at a predetermined angle, and repeating execution of irradiating the calibration tool with the X-ray, and identifying positions of feature points of projected images of the reference objects in the N places from the output of the X-ray image detector to calculating the transformation matrix from the positions of the feature points of the projected images of the reference objects in the N places and the specific relative positional intervals, the transformation matrix being used for projective transformation of the reference objects onto the detection surface of the X-ray image detector;

calculating absolute positions of the reference objects for each rotation at the predetermined angle on a basis of the transformation matrix; and calculating a rotation center position of the rotating table from change in the absolute positions of the reference objects caused by rotation of the rotating table.

2. The calibration method of an X-ray measuring device according to claim 1, wherein
in the parallelly moving of the reference objects disposed in the N places, a differential position of the position of the feature point of the projected image of the one reference object with respect to the position of the feature point of the projected image of the other reference object is calculated, and the reference objects in the N places are parallelly moved on a basis of the differential position.

3. The calibration method of an X-ray measuring device according to claim 2, wherein
when the correlation between the projected image of the one reference object and the projected image of the other reference object is maximum, a magnitude of the differential position is equal to or less than a specified value.

4. The calibration method of an X-ray measuring device according to claim 1, wherein
the rotating table is rotated a plurality of times at a specific angle, the parallelly moving of the reference objects disposed in the N places, to the calculating the specific relative positional intervals from each of the moving positions are repeatedly executed, and
an average of the plurality of specific relative position intervals obtained by the repeated execution is calculated, or positions before and after the parallel movement when the repeated execution is performed executed next time is associated with the specific relative position intervals calculated immediately before.

5. The calibration method of an X-ray measuring device according to claim 1, wherein
when all the reference objects are mounted on only one plane in the calibration tool, the transformation matrix is defined as a projective transformation matrix, and when the reference objects are mounted three-dimensionally, the transformation matrix is defined as a projection matrix.

6. The calibration method of an X-ray measuring device according to claim 1, wherein
in, the calculating a rotation center position of the rotating table, a rotary axis of the rotating table is further calculated.

7. The calibration method of an X-ray measuring device according to claim 1, wherein
in the calculating absolute positions of the reference objects, on an assumption that the X-ray source and the X-ray image detector rotate instead of the rotating table, absolute positions of the reference objects are calculated by calculating an absolute position of the X-ray source for each rotation at the predetermined angle on a basis of the transformation matrix and by transforming the absolute position of the X-ray source into coordinates.

8. The calibration method of an X-ray measuring device according to claim 7, wherein
when the absolute position of the X-ray source is calculated by rotating the rotating table three times or more at the predetermined angle, a distance between the X-ray source and the X-ray image detector and a position of a foot of a perpendicular from the X-ray source to the X-ray image detector are converted into variables, and a distance error between a position on a locus of a provisional true circle and the absolute position of the X-ray source is evaluated so as to calculate the distance between the X-ray source and the X-ray image detector and a position of the foot of the perpendicular from the X-ray source to the X-ray image detector, the provisional true circle being obtained by fitting the absolute positions of the X-ray source calculated on a basis of the transformation matrix to a true circle.

9. The calibration method of an X-ray measuring device according to claim 1, wherein
in the calculating a rotation center position of the rotating table, a center position of a locus obtained by fitting change in the absolute positions of the reference objects to a true circle is calculated, and the calculated center position is defined as the rotation center position of the rotating table.

10. The calibration method of an X-ray measuring device according to claim 9, wherein
in calculation of a rotary axis of the rotating table, an angle of inclination from a horizontal plane of the locus is further calculated, and the rotary axis is calculated from the angle of inclination and the rotation center position.

11. The calibration method of an X-ray measuring device according to claim 1, wherein
the reference objects are each a sphere.

12. The calibration method of an X-ray measuring device according to claim 1, wherein the positions of the feature points of the projected images of the reference objects are centroid positions of the projected images.

\* \* \* \* \*